US009649306B2

(12) United States Patent
Barbugian et al.

(10) Patent No.: US 9,649,306 B2
(45) Date of Patent: *May 16, 2017

(54) TREATMENT OF DISEASES THROUGH ADMINISTRATION OF N-[5-(3,5-DIFLUORO-BENZYL)-1H-INDAZOL-3-YL]-4-(4-METHYL-PIPERAZIN-1-YL)-2-(TETRAHYDRO-PYRAN-4-YLAMINO)-BENZAMIDE

(71) Applicant: NERVIANO MEDICAL SCIENCES S.R.L., Nerviano (MI) (IT)

(72) Inventors: Natale Alvaro Barbugian, Milan (IT); Romualdo Forino, Milan (IT); Tiziano Fumagalli, Trezzano Rosa (IT); Paolo Orsini, Legnano (IT)

(73) Assignee: NERVIANO MEDICAL SCIENCES S.R.L., Nerivano (MI) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 15/172,478

(22) Filed: Jun. 3, 2016

(65) Prior Publication Data

US 2016/0279125 A1    Sep. 29, 2016

Related U.S. Application Data

(63) Continuation of application No. 14/716,986, filed on May 20, 2015, now Pat. No. 9,382,235, which is a continuation of application No. 14/528,475, filed on Oct. 30, 2014, now Pat. No. 9,085,565, which is a continuation of application No. PCT/EP2013/060534, filed on May 22, 2013.

(30) Foreign Application Priority Data

May 23, 2012  (EP) ..................... 12169139

(51) Int. Cl.
*C07D 405/12* (2006.01)
*A61K 31/496* (2006.01)
*C07D 405/14* (2006.01)

(52) U.S. Cl.
CPC .......... *A61K 31/496* (2013.01); *C07D 405/12* (2013.01); *C07D 405/14* (2013.01); *C07B 2200/13* (2013.01)

(58) Field of Classification Search
None
See application file for complete search history.

(56) References Cited

U.S. PATENT DOCUMENTS

| 9,085,565 | B2* | 7/2015 | Barbugian | C07D 405/12 |
| 9,382,235 | B2* | 7/2016 | Barbugian | C07D 405/12 |
| 2015/0051222 | A1 | 2/2015 | Barbugian et al. | |
| 2015/0274707 | A1 | 10/2015 | Barbugian et al. | |

FOREIGN PATENT DOCUMENTS

WO    WO 2009/013126 A1    1/2009

OTHER PUBLICATIONS

Cohen P., "The Development and Therapeutic Potential of Protein Kinase Inhibitors", Current Opinion in Chemical Biology 3:459-465 (1999).
Cohen P., "Protein Kinases—The Major Drug Targets of the Twenty-First Century?", Nature Reviews—Drug Discovery 1:309-315 (Apr. 2002).
Shaw A.T. et al., "Targeting Anaplastic Lymphoma Kinase in Lung Cancer", Clinical Cancer Research 17(8):2081-2086 (Apr. 15, 2011).
Stephen ed., Cancer Drug Design and Discovery Neidle, (Elsevier/Academic Press), pp. 427-431 (2008).
Velculescu V.E., "Defining the Blueprint of the Cancer Genome", Carcinogensis 29(6):1087-1091 (2008).
Warner S.L. et al., "Targeting Aurora-2 Kinase in Cancer", Molecular Cancer Therapeutics 2:589-595 (Jun. 2003).
Weroha S.J. et al., "IGF-1 Receptor Inhibitors in Clinical Trials—Early Lessons", J Mammary Gland Biol Neoplasia. 13(4):471-483 (Dec. 2008).
International Search Report dated Jul. 22, 2013 received from Application No. PCT/EP2013/060534.
U.S. Office Action dated Dec. 17, 2014 issued in corresponding U.S. Appl. No. 14/528,475.
U.S. Office Action dated Sep. 25, 2015 issued in corresponding U.S. Appl. No. 14/716,986.

* cited by examiner

*Primary Examiner* — Emily Bernhardt
(74) *Attorney, Agent, or Firm* — Scully, Scott, Murphy & Presser, P.C.

(57) ABSTRACT

The present invention relates to a process for the preparation of N-[5-(3,5-difluoro-benzyl)-1H-indazol-3-yl]-4-(4-methyl-piperazin-1-yl)-2-(tetrahydro-pyran-4-ylamino)-benzamide. Novel solid forms of this compound, their utility in treating diseases caused by deregulated protein kinase activity and pharmaceutical compositions containing them are also object of the present invention.

10 Claims, 8 Drawing Sheets

Crystalline Form 1

TREATMENT OF DISEASES THROUGH ADMINISTRATION OF N-[5-(3,5-DIFLUORO-BENZYL)-1H-INDAZOL-3-YL]-4-(4-METHYL-PIPERAZIN-1-YL)-2-(TETRAHYDRO-PYRAN-4-YLAMINO)-BENZAMIDE

CROSS-REFERENCE TO RELATED APPLICATIONS

The present application is a continuation of co-pending application having U.S. Ser. No. 14/716,986; filed on May 20, 2015, which is a continuation of a co-pending application having U.S. Ser. No. 14/528,475, filed on Oct. 30, 2014, now U.S. Pat. No. 9,085,565; which is a continuation of International Application No. PCT/EP2013/060534, filed on May 22, 2013, which claims priority to European Application No. 12169139.8, filed on May 23, 2012; the contents of all of which are incorporated here by reference.

The present invention relates to a process for the preparation of N-[5-(3,5-difluoro-benzyl)-1H-indazol-3-yl]-4-(4-methyl-piperazin-1-yl)-2-(tetrahydro-pyran-4-ylamino)-benzamide. Novel solid forms of this compound, their utility in treating diseases caused by deregulated protein kinase activity and pharmaceutical compositions containing them are also object of the present invention.

The malfunctioning of protein kinases (PKs) is the hallmark of numerous diseases. A large share of the oncogenes and proto-oncogenes involved in human cancers encode for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis, glomerulonephritis and post-surgical stenosis and restenosis. PKs are also implicated in inflammatory conditions and in the multiplication of viruses and parasites. PKs may also play a major role in the pathogenesis and development of neurodegenerative disorders.

For a general reference to PKs malfunctioning or deregulation see, for instance, Current Opinion in Chemical Biology 1999, 3, 459-465; Nature Rev. Drug Discov. 2002; and Carcinogenesis 2008, 29, 1087-1091. A subset of PK is a group of membrane receptors with intrinsic protein-tyrosine kinase activity (RPTK). Upon binding of growth factors, RPTKs become activated and phosphorylate themselves and a series of substrates in the cytoplasm. Through this mechanism, they can transduce intracellular signallings for proliferation, differentiation or other biological changes. Structural abnormalities, over-expression and activation of RTPKs are frequently observed in human tumors, suggesting that constitutive ignition of the signal transduction leading to cell proliferation can result in malignant transformation. Anaplastic lymphoma kinase (ALK) is a tyrosine kinase receptor belonging to the insulin receptor subfamily of RTKs: the ALK gene is located on cromosome 2 and is expressed mainly in neuronal cells, especially during development. The ALK gene is involved in a balanced chromosomal translocation with the Nucleophosmin (NPM) gene on cromosome 5 in a large subset of Anaplastic Large Cell Lymphomas (ALCL). In the ALK+ALCL, as a result of the translocation, the NPM ubiquitous promoter drives an ectopic expression of the fusion protein in which the NPM moiety dimerizes and the ALK kinase domain undergoes auto-phosphorylation and becomes constitutively active.

Many data from the literature have demonstrated that the NPM-ALK fusion protein has a strong oncogenic potential and its ectopic expression is responsible for cellular transformation. Moreover, the constitutive expression of human NPM ALK in mouse T-cell lymphocytes is sufficient for the development of lymphoid neoplasia in transgenic animals with a short period of latency.

ALCL is a defined disease characterized by the surface expression of the CD30 antigen (Ki-1), and accounts for 2% of adult and 13% of pediatric non-Hodgkin's lymphomas, affecting predominantly young male patients. ALK+ ALCL accounts for 70% of all ALCLs and is an aggressive disease with systemic signs, and frequent extranodal involvement (bone marrow, skin, bone, soft tissues).

About 15-20% of ALK-expressing ALCLs were found to bear a different chromosomal translocation, involving the cytoplasmic portion of ALK, with different N-terminal moieties, all resulting in constitutive activation of the ALK kinase domain.

Moreover, cell lines established from solid tumors of ectodermal origin like melanomas, breast carcinomas, as well as neuroblastomas, glioblastomas, Ewings sarcomas, retinoblastomas, were found to express the ALK receptor.

In conclusion, interfering with the ALK signalling likely represents a specific and effective way to block tumor cell proliferation in ALCL and possibly other indications.

The international patent application WO2009/013126 (Nerviano Medical Sciences Sri.) describes and claims the free-base form of N-[5-(3,5-Difluoro-benzyl)-1H-indazol-3-yl]-4-(4-methyl-piperazin-1-yl)-2-(tetrahydro-pyran-4-ylamino)-benzamide, which has formula (I),

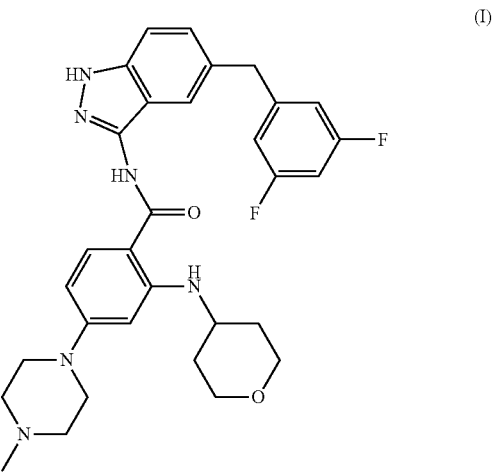 [SMILES: CN1CCN(c2ccc(C(=O)Nc3n[nH]c4ccc(Cc5cc(F)cc(F)c5)cc34)c(NC3CCOCC3)c2)CC1]

and reports that the compound is active as a kinase inhibitor, more particularly as ALK inhibitor, and it is thus useful in the treatment of a variety of cancers and cell proliferative disorders.

The preparations of this compound are described in example 2 (step i') and in example 7 of the above noted patent application.

The known preparation of the compound of formula (I), as described in example 2 (step i') of the above noted patent application comprises, essentially, adding a solution of 5-(3,5-difluoro-benzyl)-1H-indazol-3-ylamine to the 4-(4-methyl-piperazin-1-yl)-2-[(tetrahydro-pyran-4-yl)-(2,2,2-trifluoro-acetyl)-amino]-benzoic acyl chloride, and then deprotecting with an organic base at high temperature the obtained compound to give the desired amide of formula (I), after purification by column chromatography and crystallization.

The known preparation of the compound of formula (I) as described in example 7 of the above noted patent application comprises, essentially, reacting 2-amino-N-[5-(3,5-difluorobenzyl)-1H-indazol-3-yl]-4-(4-methyl-piperazin-1-yl)-benzamide with tetrahydro-pyran-4-one in presence of trifluoroacetic acid and tetramethylammonium triacetoxyborohydride to give the desired amide of formula (I), after purification by column chromatography.

In this respect, we have now surprisingly found that the compound of formula (I) can be advantageously prepared through a process which allows obtaining the desired product in an industrially advantageous and highly reproducible manner, with high purity, with characteristics suitable for administration to humans and at a reduced cost. In addition, the new process is more suitable for application in large-scale production. Finally, said compound is obtained in defined solid forms.

Therefore, it is a first object of the present invention a process for preparing the compound of formula (I) as defined above, which process comprises:

a) adding in a stoichiometric manner the acyl chloride of formula (II):

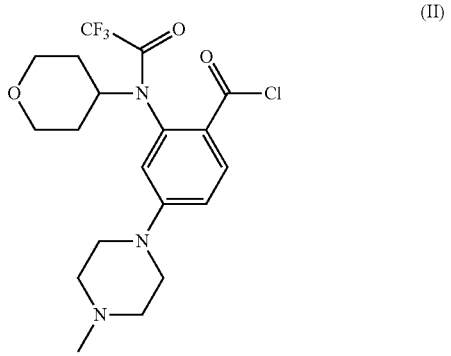 [SMILES: CN1CCN(c2ccc(C(=O)Cl)c(N(C(=O)C(F)(F)F)C3CCOCC3)c2)CC1]

to the indazol-3-ylamine of formula (III):

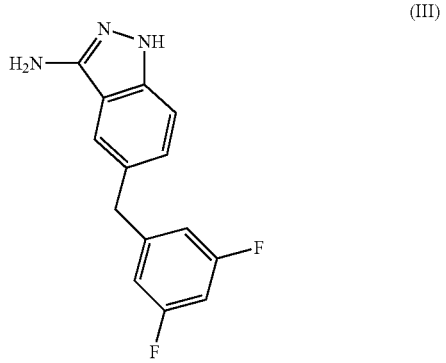 [SMILES: Nc1n[nH]c2ccc(Cc3cc(F)cc(F)c3)cc12]

blocking the addition when the indazol-3-ylamine of formula (III) is completely reacted;

b) deprotecting under mild basic conditions the resulting compound of formula (IV):

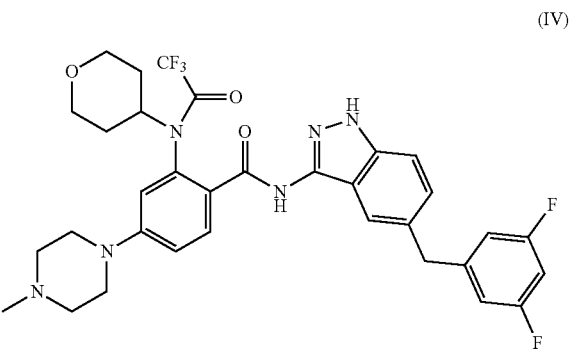 [SMILES: CN1CCN(c2ccc(C(=O)Nc3n[nH]c4ccc(Cc5cc(F)cc(F)c5)cc34)c(N(C(=O)C(F)(F)F)C3CCOCC3)c2)CC1]

to obtain the desired compound of formula (I), which is isolated in amorphous form;

the desired crystalline form is then obtained either c1) treating the resultant amorphous compound of formula (I) with a mixture of ethanol and water in presence of seeds, to give the desired compound of formula (I) in crystalline form 1 or c2) treating the resultant amorphous compound of formula (I) with a mixture of ethanol and water, to give the desired compound of formula (I) in crystalline form 2, and optionally d) converting the resultant compound obtained in step b), in step c1) or in step c2) into a pharmaceutically acceptable salt.

The new procedure allows obtaining a compound of formula (I) with high purity without chromatographic purifications and controlling the solid form.

Due to the order of addition and to the stoichiometric addition of the acyl derivative of formula (II) to the indazolylamine derivative of formula (III), followed by an isolation work up with appropriate solvents mixture, the protected intermediate of formula (IV) obtained in step a) is purer than in the previous process. As a matter of facts, this new procedure considerably reduces the formation of impurities, such as for example the formation of undesired regioisomers and products of double addition, thus avoiding the need to purify the so obtained product of formula (IV) by the use of chromatography columns, not suitable for large-scale preparations because of the time and costs associated with this procedure.

Furthermore, in step b), transforming the product of formula (IV) into the final product of formula (I), the mild deprotection conditions consisting of low temperature aqueous hydrolysis with inorganic bases, prevent the by-products formation observed in the previous procedure due to the high temperature treatment with organic bases in methanol.

Finally in step c1) or step c2) the compound of formula (I), obtained at first in an amorphous form, is then converted respectively in crystalline form 1 by seeding or in crystalline form 2 by treatment with the appropriate solvents. In the previous process at this point, the purity of the compound and the isolation procedures by insolubilization and/or by chromatographic purification were such to prevent the conversion to either crystalline form 1 or crystalline form 2.

According to step a), the compound of formula (II) is suspended in solvents such as THF or DCM, preferably it is suspended in dry DCM, and then the suspension is added slowly and gradually to a solution of the compound of formula (III) in pyridine.

Preferably the reaction is carried out at a temperature between −20° C. and −40° C., preferably operating at a temperature between −30° C. and −40° C.

At the reaction end, solvents are evaporated and the residue treated with solvents like DMC, MTBE, MeOH in a predefined ratio between 1/1/1 and 30/30/1, preferably the treatment is made with ratios DCM/MTBE/MeOH between 8/8/1 and 30/30/1, to obtain the precipitation of a pure compound of formula (IV).

According to step b), the deprotection of the compound of formula (IV) may be carried out by mild basic conditions such as aqueous or aqueous/methanolic alkaline carbonates or hydroxides, preferably a solution of $K_2CO_3$ in water/methanol is used.

Preferably the reaction is carried out at a temperature between 20° C. and 5° C., preferably operating at about 10° C.

The desired compound of formula (I) is then isolated in amorphous form by dropping into water, at a temperature between 5° C. and 25° C., preferably at a temperature between 5° C. and 10° C.

According to stop c1) the amorphous compound of formula (I) is treated at first with ethanol heating to reflux and distilling part of the solvent, then with water and crystalline form 1 seeds at a temperature between 10° C. and 30° C., preferably at a temperature between 20° C. and 25° C. The obtained compound of formula (I) is in crystalline form 1.

According to step c2) the product obtained according to step b) is treated sequentially with ethanol, at a temperature between 10° C. and 30° C., preferably at a temperature between 20° C. and 25° C., and then with water at a temperature between 10° C. and 30° C., preferably at a temperature between 20° C. and 25° C. The obtained compound of formula (I) is in crystalline form 2.

The starting compounds and the reagents employed in the process of the present invention are known compounds or can be obtained from known compounds using well known methods. In particular, the preparation of the compounds of formula (II) and (III) as defined above is described in the above cited patent application.

No solid form, amorphous or crystal, is mentioned in example 2 (step i') and in example 7 of the above noted patent application. The present inventors have studied and found that the compound of formula (I) prepared as described in example 2 (step i') is a crystal solvate that hereinafter is referred to as crystalline form 3 for convenience; the compound of formula (I) prepared as described in example 7 is amorphous and hereinafter is referred to as amorphous form.

Moreover, the present inventors have found that the compound of formula (I) prepared as described in example 1, step b) of the present application is amorphous; the compound of formula (I) prepared as described in example 1, step c1) of the present application is a crystal that hereinafter is referred to as crystalline form 1; finally the compound of formula (I) prepared as described in example 1, step c2) of the present application is a crystal that hereinafter is referred to as crystalline form 2.

Then, in a further aspect, the present invention relates to novel and stable crystalline forms of the compound of formula (I), i.e. crystalline form 1 and crystalline form 2, prepared by the process described above.

Crystalline form 3 is a solvate with EtOAc and n-hexane and is not suitable for human administration due to the presence of unacceptable amounts of solvents; the amorphous form is a hygroscopic solid, that is less suitable for development of an oral formulation.

Moisture uptake is a significant concern for pharmaceutical powders. Moisture has been shown to have a significant impact, for example, on the physical, chemical and manufacturing properties of drugs, excipients and formulations. It is also a key factor in taking decisions related to packaging, storage, handing and shelf life and successful development requires a sound understanding of hygroscopic properties.

For instance, conversion from an anhydrous to a hydrate form may be observed when the relative humidity exceeds a critical level and moisture content rapidly increases in the solid. This has not only an impact on the physical and pharmaceutical properties of the drug per se, but also on its biopharmaceutical perspective. Moreover, it is well known, that hydrate forms usually tends to be less soluble with respect to a homologous anhydrous form, with potential detrimental effect also on the dissolution rate properties of the active compound per se and on its absorption profile through the gastrointestinal tract. At the same manner, conversion from an amorphous form to a crystalline form may be observed in presence of humidity, with potential disadvantages in terms of physical stability. The amorphous active drug substance, if deliquescent, can for instance absorb relatively large amounts of water from the atmosphere up to its dissolution while also its chemical stability can be affected since the amorphous structure, being thermodynamically activated, is more prone to chemical degradation and to chemical interaction with other chemical species. Thus the performance and the efficacy of both formulation and active ingredient may be significantly changed.

Accordingly, there is a need in therapy of solid forms of the compound of formula (I) suitable for human administration that do not contain unacceptable amounts of residual solvents and endowed with low hygroscopicity, as well as good and reproducible biopharmaceutical properties for allowing a safer and efficacious oral administration.

The present inventors have solved the above-described technical problem by providing novel crystalline forms of the compound of formula (I) being suitable for human administration and having improved physicochemical properties. In fact, the novel crystalline forms do not retain solvents and are less hygroscopic than the amorphous form, in addition to possessing all the other advantages, in particular therapeutic advantages, exhibited by the known forms.

BRIEF DESCRIPTION OF THE DRAWINGS

The invention is also illustrated by reference to the accompanying drawings described below.

2-Theta angles (deg) are reported on the x axis while intensity (CPS) is reported on they axis.

Figure 2:
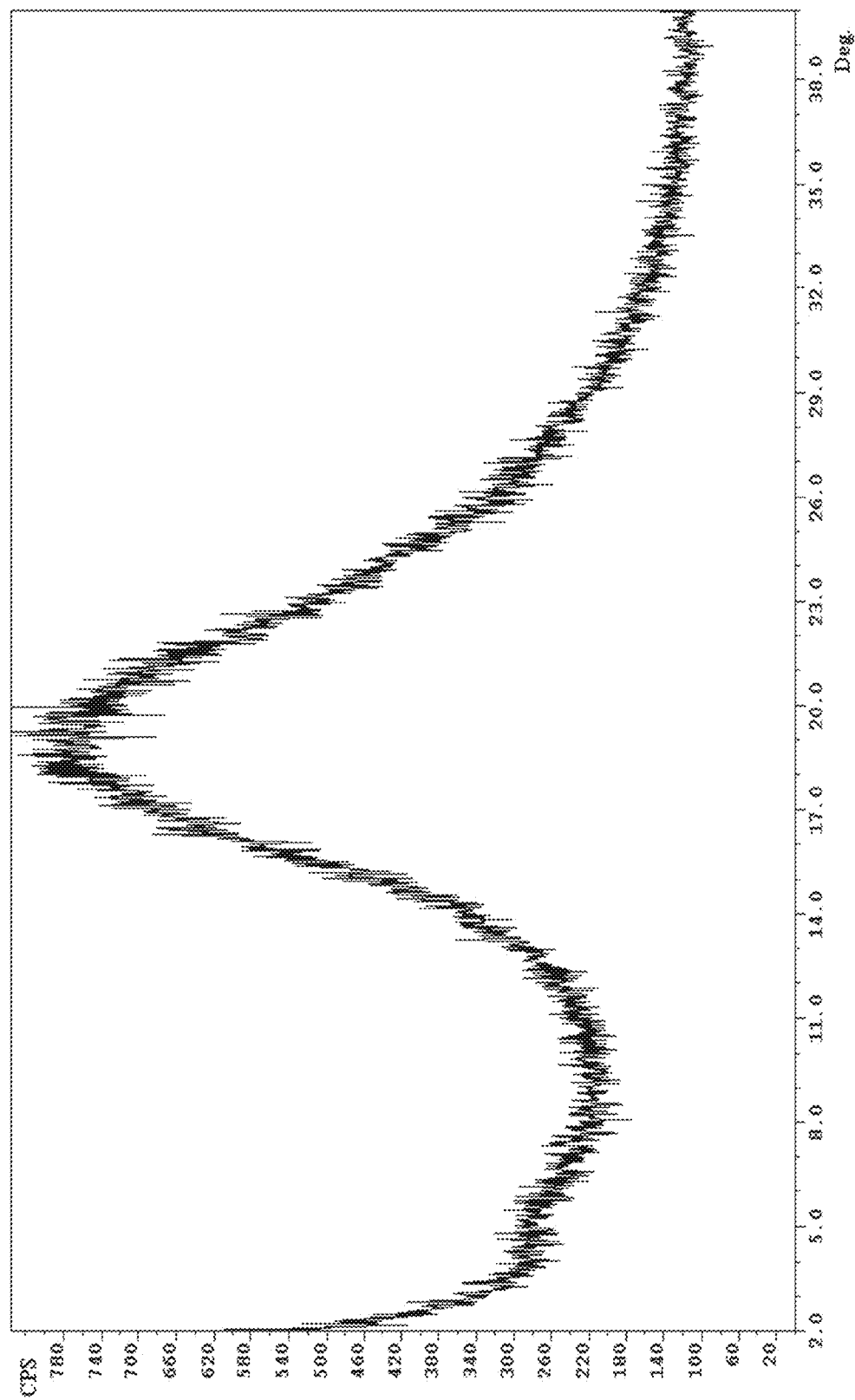

FIG. 2 shows the X-ray diffractograms of the amorphous form.

2-Theta angles (deg) are reported on the x axis while intensity (CPS) is reported on the y axis.

Figure 3:
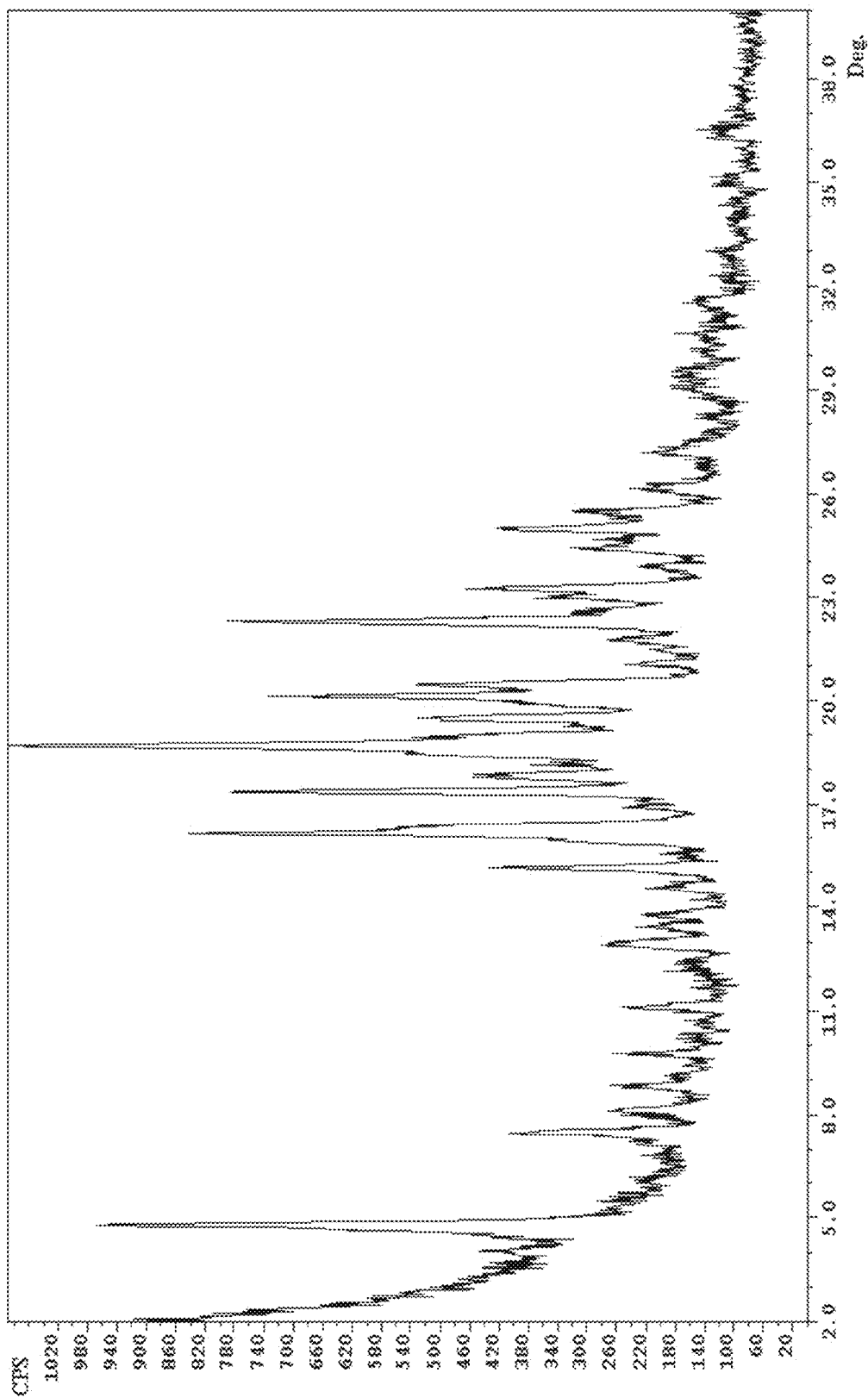

FIG. 3 shows the X-ray diffractograms of the crystalline form 1.

2-Theta angles (deg) are reported on the x axis while intensity (CPS) is reported on the y axis.

Figure 4:
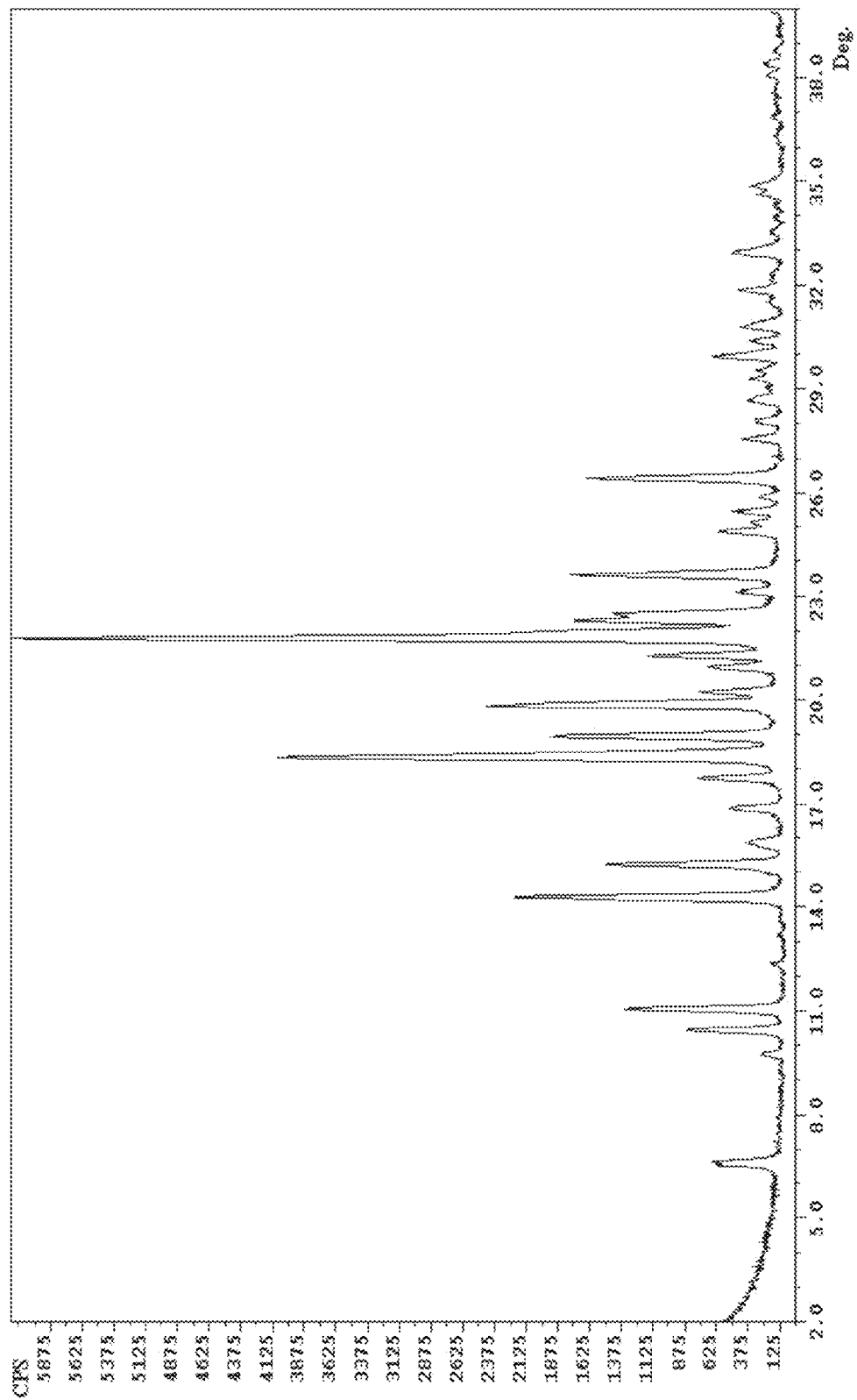

FIG. 4 shows the X-ray diffractograms of the crystalline form 2.

2-Theta angles (deg) are reported on the x axis while intensity (CPS) is reported on they axis.

Figure 5:
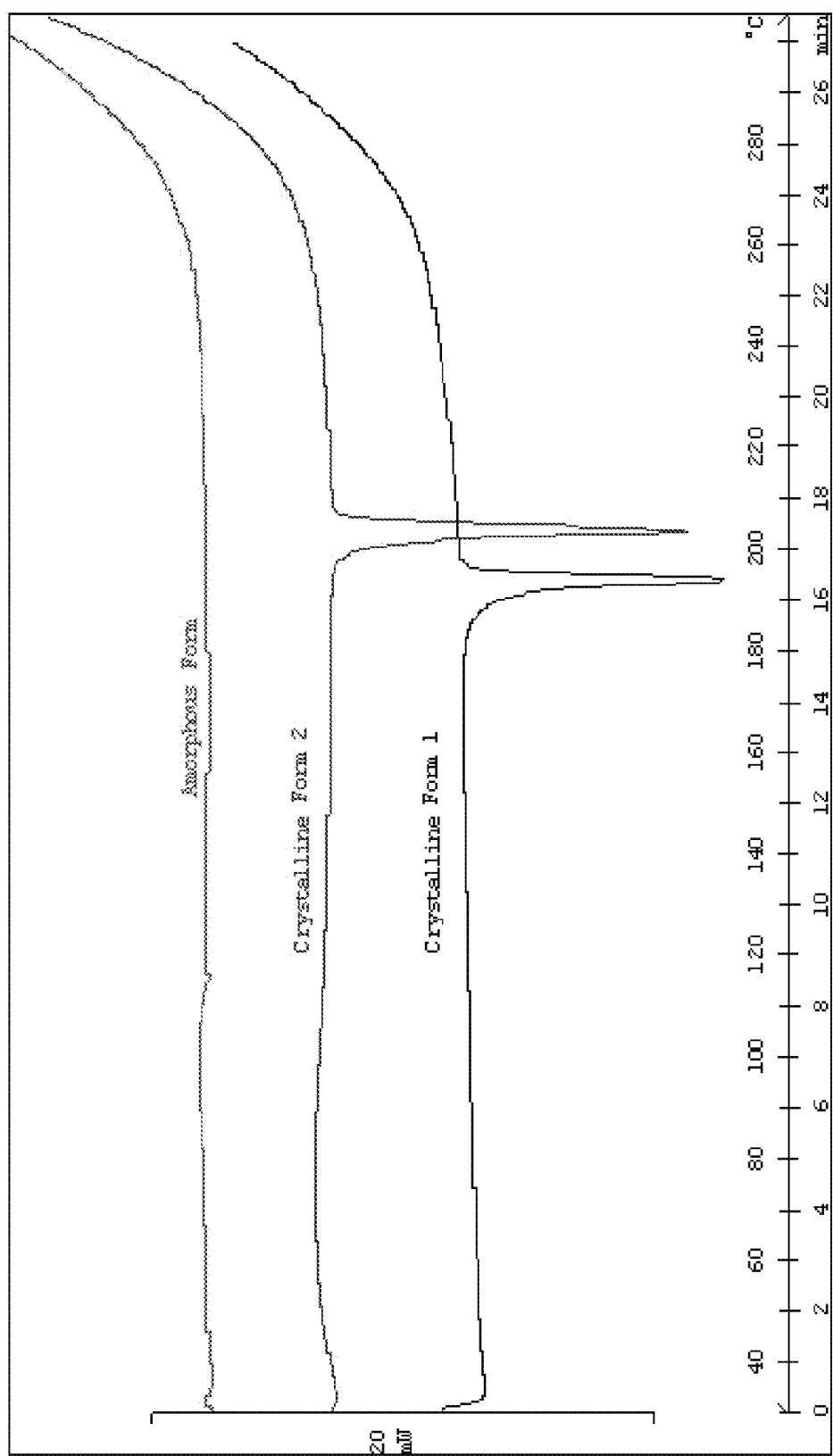

FIG. 5 shows the DSC thermograms of the amorphous form, crystalline form 1 and crystalline form 2.

The thermogram reports temperature (° C.) and time (min) on the x axis while heat flow (mW) is reported on the y axis.

Figure 6:
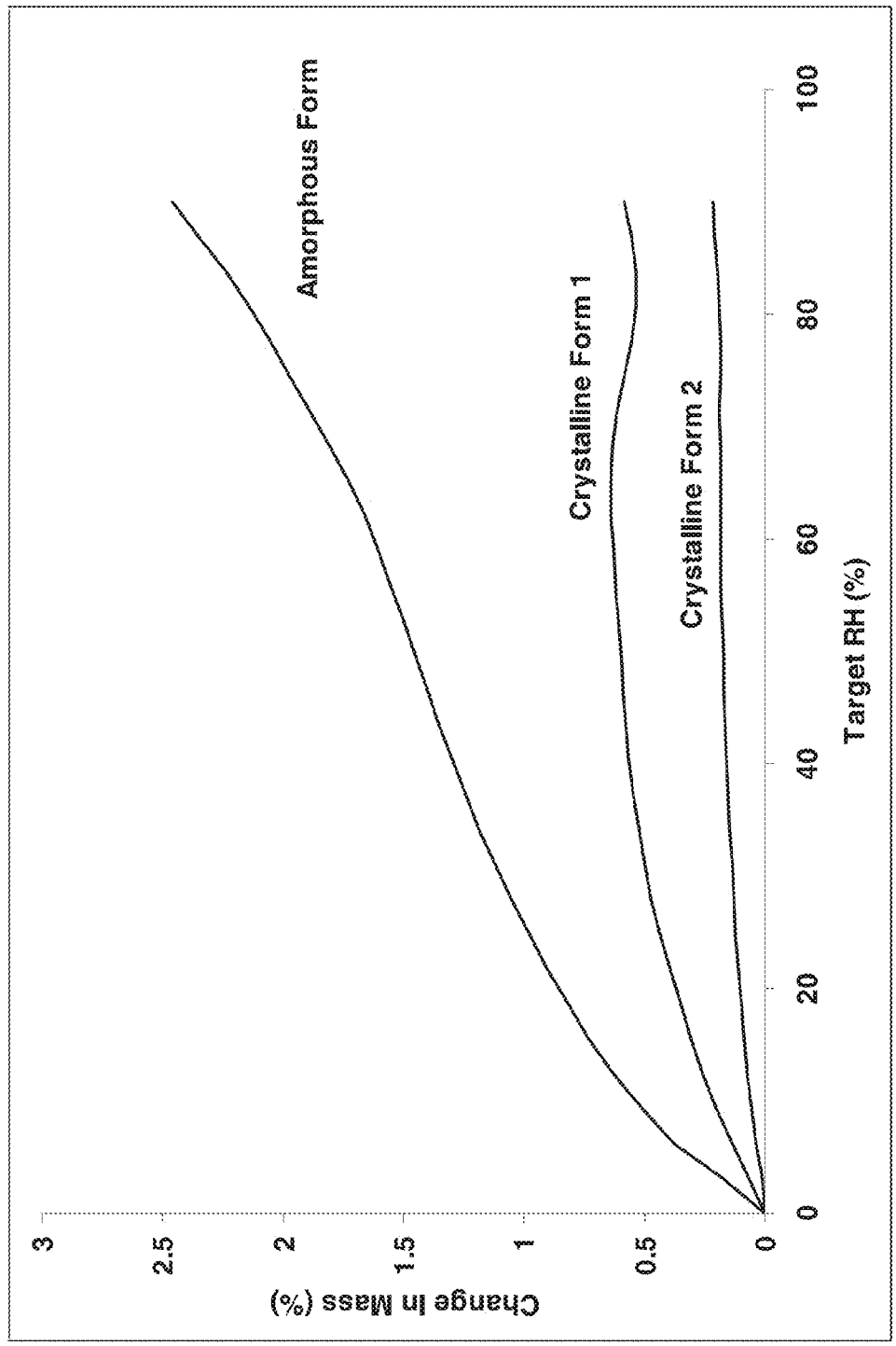

FIG. 6 shows the DVS isotherm plot of the amorphous form, crystalline form 1 and crystalline form 2.

Relative Humidity (RH, %) values are reported on the x axis while Change In Mass (%) is reported on the y axis. The curves are related to the sorption step between 0% RH and 90% RH at 25° C.

Figure 7:
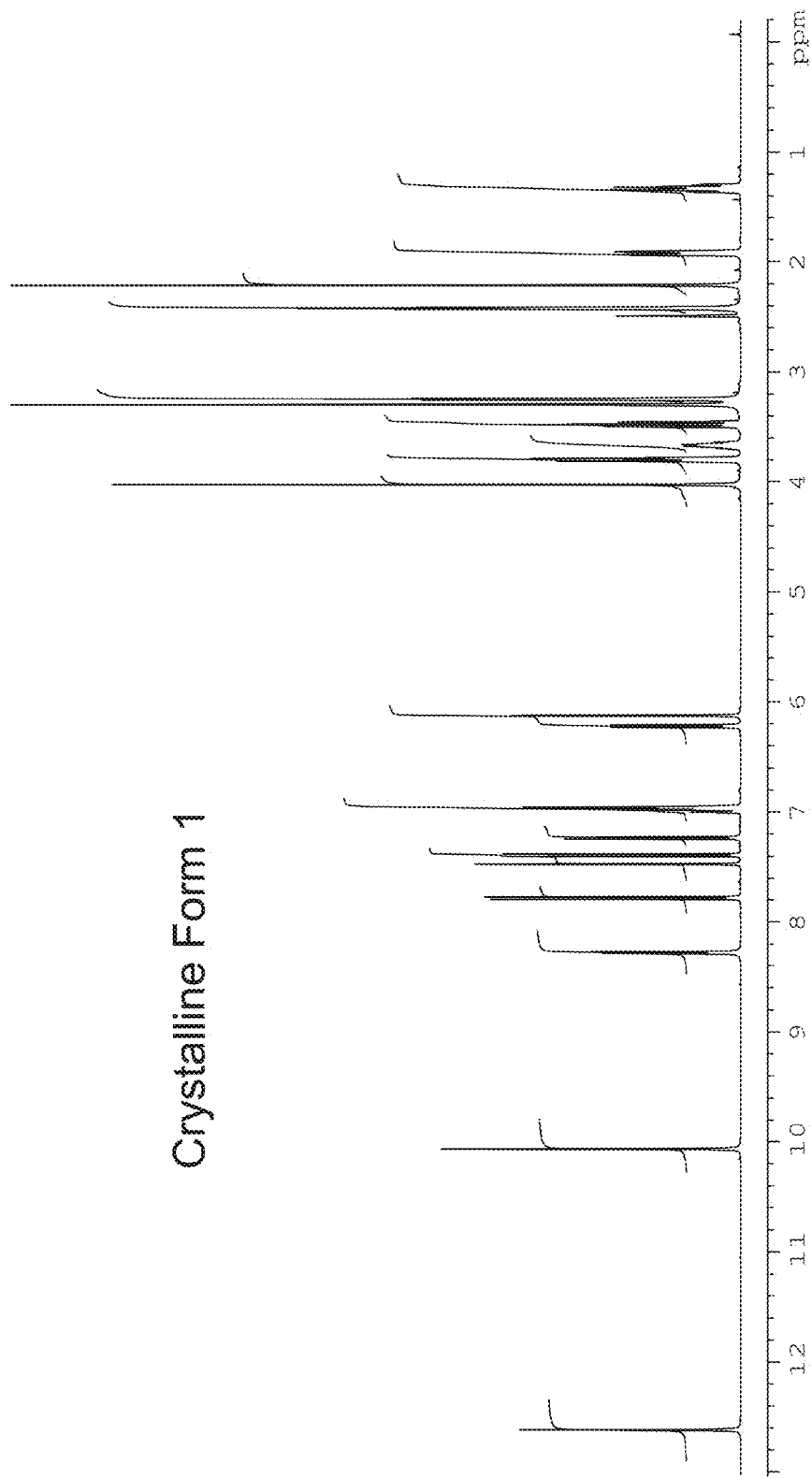

FIG. 7 shows the $^1$H NMR spectrum of the crystalline form 1.

Chemical shift (ppm) is reported on the x axis.

Figure 8:
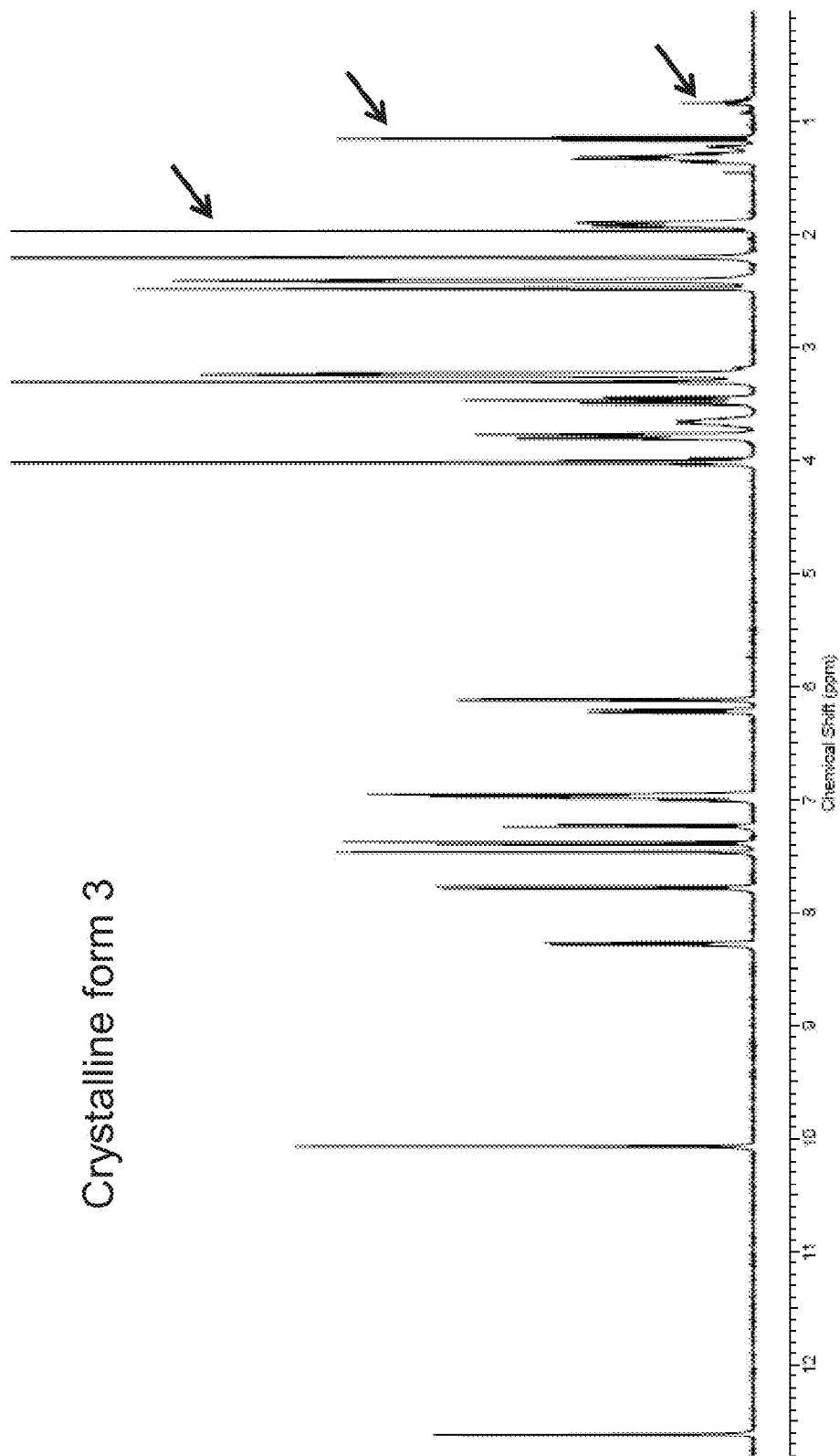

FIG. 8 shows the $^1$H NMR spectrum of the crystalline form 3.

Chemical shift (ppm) is reported on the x axis.

Figure 1:
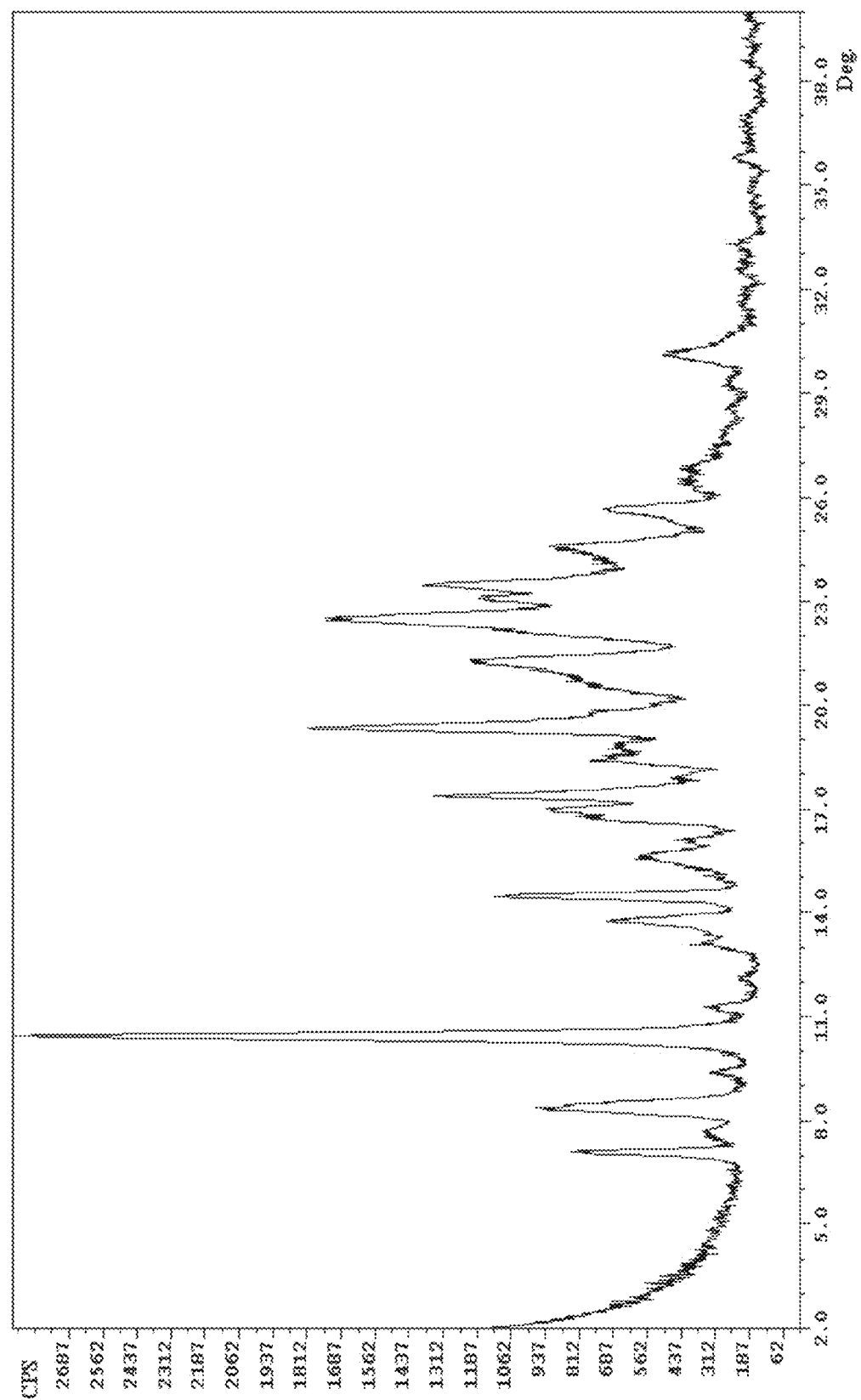
FIG. 1 shows the X-ray diffractograms of the crystalline form 3.

The crystalline form 3 is characterized by an X-ray diffraction diagram that is substantially the same as the diagram reported in FIG. 1, with significant peak intensities at about the 2-theta values (deg) described in table 1. In samples being free of any additional materials (other crystalline forms, excipients), it should be possible to observe diffraction peaks at about the 2-theta values (deg) described in table 2.

The amorphous form is characterized by an X-ray diffraction diagram that is substantially the same as the diagram reported in FIG. 2.

The crystalline form 1 is characterized by an X-ray diffraction diagram that is substantially the same as the diagram reported in FIG. 3, with significant peak intensities at about the 2-theta values (deg) described in table 1. In samples being free of any additional materials (other crystalline forms, excipients), it should be possible to observe diffraction peaks at about the 2-theta values (deg) described in table 3.

The crystalline form 2 is characterized by an X-ray diffraction diagram that is substantially the same as the diagram reported FIG. 4, with significant peak intensities at about the 2-theta values (deg) described in table 1. In samples being free of any additional materials (other crystalline forms, excipients), it should be possible to observe diffraction peaks at about the 2-theta values (deg) described in table 4.

As a further aspect it has been found that crystalline form 3 is a high melting crystalline form of compound of formula (I) showing solvation with ethyl acetate and n-hexane (PXRD profile: FIG. 1; other references about PXRD are described in table 1).

As a further aspect it has been found that amorphous form shows a water uptake of 2.5% at 25° C./90% RH that is reversible by lowering RH at constant temperature of 25° C. (PXRD profile: FIG. 2; DSC profile: FIG. 5; DVS profile: FIG. 6; other references about PXRD, DSC and DVS profiles are described in table 1).

As a further aspect it has been found that crystalline form 1 is a high melting crystalline form of compound of formula (I), that shows a water uptake of 0.6% at 25° C./90% RH that is lower than the amorphous form and reversible by lowering RH at constant temperature of 25° C. (PXRD profile: FIG. 3; DSC profile: FIG. 5; DVS profiles; FIG. 6; other references about PXRD, DSC and DVS profiles are described in table 1).

As a further aspect it has been found that crystalline form 2 is a high melting crystalline form of compound of formula (I), that shows a water uptake of 0.2% at 25° C./90% RH that is lower than the amorphous form and reversible by lowering RH at constant temperature of 25° C., (PXRD profile: FIG. 4; DSC profile: FIG. 5; DVS profiles: FIG. 6; other references about PXRD, DSC and DVS profiles are described in table 1).

TABLE 1

Description of the solid state properties and Figures/Table references of crystalline form 3, amorphous form, crystalline form 1 and crystalline form 2 of the compound of formula (I).

| Compound (I) | PXRD FIG. | PXRD Table | Significant PXRD peaks (2-theta, deg) (*) | DSC | DVS |
|---|---|---|---|---|---|
| Crystalline form 3 | 1 | 2 | 7.1, 8.4, 10.5, 13.8, 14.5, 16.8, 17.0, 17.4, 19.3, 20.7, 21.3, 22.5, 23.5, 24.5, 25.6. | Not applicable | Not applicable |
| Amorphous form | 2 | Not applicable | Not applicable | FIG. 5 | FIG. 6 |
| Crystalline form 1 | 3 | 3 | 4.8, 7.5, 15.2, 16.2, 17.4, 17.8, 18.7, 19.5, 20.1, 20.5, 22.3, 23.0, 23.3, 24.4, 25.0 | FIG. 5 | FIG. 6 |
| Crystalline form 2 | 4 | 4 | 10.5, 11.1, 14.3, 15.3, 17.8, 18.4, 19.0, 19.9, 21.3, 21.8, 22.3, 22.5, 23.6, 26.4, 30.0. | FIG. 5 | FIG. 6 |

Note
(*) the reported PXRD peaks have been selected according to their high intensity among the complete dataset.

A further object of the invention is to provide a pharmaceutical composition comprising a therapeutically effective amount of crystalline form 1 or crystalline form 2 as defined above, or a pharmaceutically acceptable salt thereof, as active ingredient and a pharmaceutically acceptable, excipient, carrier or diluent.

Crystalline form 1 or crystalline form 2 as defined above, or a pharmaceutically acceptable salt thereof, is readily orally absorbed, therefore it is preferably orally administered. Needless to say, the compounds of the present invention may be administered by any administration route, for instance by parenteral, topical, rectal and nasal route.

The compositions of the invention may be in a form suitable for oral use. Examples of these forms are: tablets, hard or soft capsules, aqueous or oily suspensions, emulsions, dispersible powders or granules. The compositions of the invention may also be in a form suitable for topical use. Examples of these forms are: creams, ointments, gels, or aqueous or oily solutions or suspensions. The compositions of the invention may also be in a form suitable for administration by inhalation such as, for example, finely divided powder or a liquid aerosol. The compositions of the invention may also be in a form suitable for administration by insufflation such as, for example, finely divided powder. The compositions of the invention may also be in a form suitable for parenteral administration (such as, for example, a sterile aqueous or oily solution for intravenous, subcutaneous, intramuscular) or as a suppository for rectal dosing.

The compositions of the invention may be obtained by conventional procedures using conventional pharmaceutical excipients, well known in the art.

Thus, compositions intended for oral use may contain one or more additives such as, for example, colouring, sweetening, flavouring and preservative agents.

For example, the solid oral forms may contain, together with the active compound, diluents, e.g., lactose, dextrose, saccharose, sucrose, mannitol, cellulose, corn starch or potato starch; lubricants, e.g., silica, talc, stearic acid, magnesium or calcium stearate, and/or polyethylene glycols; glidants, e.g. colloidal silicon dioxide; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

A further object of the invention is to provide crystalline form 1 or crystalline form 2 as defined above, or a pharmaceutically acceptable salt thereof, for use as a medicament.

A further object of the invention is to provide crystalline form 1 or crystalline form 2, as defined above, or a pharmaceutically acceptable salt thereof, either alone or in association with other therapeutic agents or radiotherapy, for use in the treatment of a disease state treatable by ALK inhibition, such as cancer and cell proliferative disorders.

A further object of the invention is to provide a method for treating a mammal, including a human being, in need of ALK inhibition comprising administering to said mammal a therapeutically effective amount of crystalline form 1 or crystalline form 2 as defined above, or a pharmaceutically acceptable salt thereof.

Finally, another object of the invention is to provide the use of the crystalline form 1 or crystalline form 2 as defined above, or a pharmaceutically acceptable salt thereof, either alone or in association with other therapeutic agents or radiotherapy, for the manufacture of a medicament for the treatment of a disease state treatable by ALK inhibition, such as cancer and cell proliferative disorders.

The term "disease state treatable" means that the treatment according to the invention provides remission of the disease state or at least the conditions and quality of life of the mammal under treatment are improved.

Examples of such disease states are in particular different cancers that may include specific types of cancer including carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratocanthomas, thyroid follicular cancer and Kaposi's sarcoma.

Other preferred disease states are specific types of cancer such as, but not restricted to, breast cancer, lung cancer, colorectal cancer, prostate cancer, ovarian cancer, endometrial cancer, gastric cancer, clear cell renal cell carcinoma, uveal melanoma, multiple myeloma, rhabdomyosarcoma, Ewing's sarcoma, Kaposi's sarcoma, and medulloblastoma.

Other preferred disease states are ALK+ Anaplastic Large Cell Lymphomas (ALCL) and possibly other indications in which the ALK activity might play a role, like neuroblastoma, rhabdomyosarcoma, glioblastoma, inflammatory myofibroblastic tumor, and some kind of melanomas, breast carcinomas, Ewing's sarcomas, retinoblastomas and non-small cell lung carcinomas (NSCLC).

Further preferred disease states are cell proliferative disorders such as, but not restricted to, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

The term "other therapeutic agents" can include, but is not limited to, antihormonal agents such as antiestrogens, antiandrogens and aromatase inhibitors, topoisomerase I inhibitors, topoisomerase II inhibitors, agents that target microtubules, platin-based agents, alkylating agents, DNA damaging or intercalating agents, antineoplastic antimetabolites, other kinase inhibitors, other anti-angiogenic agents, inhibitors of kinesins, therapeutic monoclonal antibodies, inhibitors of mTOR, histone deacetylase inhibitors, farnesyl transferase inhibitors, and inhibitors of hypoxic response.

The effective dose of the compound of formula (I), crystalline form 1 or crystalline form 2 as defined above, or a pharmaceutically acceptable salt, may vary according to the disease, severity of the disorder and the conditions of the patient to be treated. Therefore the physician, as always, must set the optimal dose for each patient. Anyway, the effective dosage range may be from about 10 mg to about 1 g per dose (calculated as a free base), from 1 to 3 times daily.

EXAMPLES

The following Examples illustrate the invention.
Temperatures are measured in degrees Celsius (° C.).
Unless otherwise indicated, the reactions or experiments take place at room temperature.
Abbreviations:
RT: room temperature
RH: relative humidity
PXRD: Powder X-Ray diffraction
DSC: Differential Scanning Calorimetry
DVS: Dynamic Vapor Sorption
TGA: Thermogravimetric Analysis
ACN (acetonitrile)
EtOAc (Ethyl acetate)
DCM (dichloromethane)
DMA (N,N-dimethylacetamide)
DMF (N,N-dimethylformamide)
DMSO (dimethylsulfoxide)
MTBE (methyl tert-butyl ether)
THF (tetrahydrofuran)
TFA (trifluoroacetic acid)

Example 1

Preparation of the Crystalline Form 1 and Crystalline Form 2 of the Compound of Formula (I)

Scheme 1 below shows the preparation of the crystalline form 1 and crystalline form 2 of the compound of formula (I).

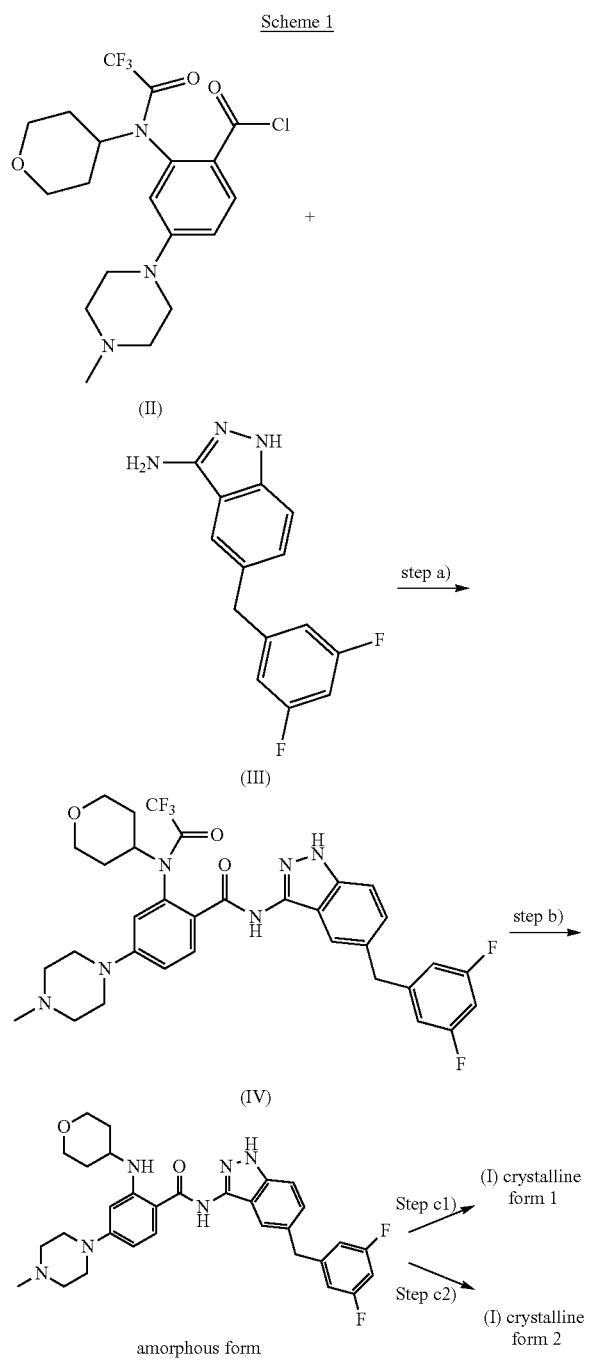

Scheme 1

To a suspension of 4-(4-methylpiperazin-1-yl)-2-[tetrahydro-2H-piran-4-yl(trifluoroacetyl)-amino]-benzoic acid trifluoroacetate (3.7 Kg, 7 mol) in dry DCM (36 L) and N,N-dimethylformamide (14 mL), oxalyl chloride (1.78 L, 21 mol) is added. The mixture is stirred for about 1.5 hours and evaporated to oily residue; dry DCM is then added and evaporated twice.

The acyl chloride of formula (II) is suspended in dry DCM and the suspension is added slowly and gradually to a solution of 5-(3,5-difluoro-benzyl)-1H-indazol-3-ylamine (1.6 Kg, 6.1 mol) in dry pyridine (16 L) at −40/−30° C. The addition is blocked when the 5-(3,5-difluoro-benzyl)-1H-indazol-3-ylamine is completely reacted. After about 1 hour the solvent is evaporated and DCM (55 L), methanol (6.5 L), and MTBE (55 L) are sequentially added. The purified protected compound of formula (IV) is filtered, washed with a mixture 10/10/1 of DCM/MTBE/MeOH and dried under vacuum (3.8 Kg).

The so obtained crude N-[5-(3,5-difluorobenzyl)-1H-indazol-3-yl]-4-(4-methyl-piperazin-1-yl)-2-[(tetrahydro-pyran-4-yl)-2,2,2-trifluoro-acetyl)-amino]-benzamide, with HPLC purity >95%, is dissolved in methanol and added with a solution of $K_2CO_3$ in water/methanol at 10° C. The solution is filtered and dropped into water; the precipitate amorphous N-[5-(3,5-difluorobenzyl)-1H-indazol-3-yl]-4-(4-methyl-piperazin-1-yl)-2-(tetrahydro-pyran-4-ylamino)-benzamide is filtered, washed with water and dried under vacuum (2.88 Kg). 5.5 g of the dried amorphous N-[5-(3,5-difluorobenzyl)-1H-indazol-3-yl]-4-(4-methyl-piperazin-1-yl)-2-(tetrahydro-pyran-4-ylamino)-benzamide are suspended in 130 mL of ethanol and heated to reflux for 10 minutes; about 70 mL of ethanol are distilled before cooling to room temperature. 110 mL of water are added and the suspension is seeded with 55 mg of crystalline form 1. The suspension is stirred for about 72 hours sampling to monitor conversion into crystalline form 1 by DSC. The suspension is then filtered and dried to give 4.3 g of the desired crystalline form 1.

The dried amorphous N-[5-(3,5-difluorobenzyl)-1H-indazol-3-yl]-4-(4-methyl-piperazin-1-yl)-2-(tetrahydro-pyran-4-ylamino)-benzamide (2.88 Kg) is slurred in about 10 volumes of ethanol to allow conversion to the desired crystalline form 2; 20 volumes of water are then added and the suspension is filtered. The product is finally dried under vacuum so giving about 2.6 Kg of N-[5-(3,5-difluorobenzyl)-1H-indazol-3-yl]-4-(4-methyl-piperazin-1-yl)-2-(tetrahydro-pyran-4-ylamino)-benzamide (4.6 mol) in the desired crystalline form 2.

Example 2

Analytical Results Means of Powder X-Ray Diffraction (PXRD)

The crystalline form 3, amorphous form, crystalline form 1 and crystalline form 2 of compound (I), were characterized by powder X-Ray Diffraction (PXRD) performed using a Thermo/ARL XTRA apparatus, irradiating powder samples with a CuKα source (45 kV, 40 mA, 1.8 kW-Kα1 radiation, wavelength λ=1.54060 Angstrom) between 2° and 40° 2-theta at room temperature.

The scan rate was of 1.20°/min (0.020° step with count time of 1 seconds per step). In the X-Ray diffractograms, the angles of diffraction 2-theta are plotted on the horizontal axis (x-axis) and the line intensity on the vertical (y-axis).

In the paragraphs defining the X-ray powder diffraction peaks for the crystalline forms of compound of formula (I), the term 'at about' is used in the expression ' . . . at about 2-theta angles reported in table . . . ' to indicate that the precise positions of peaks (i.e. the recited 2-theta angle values) should not be considered as being absolute values because, as will be appreciated by those skilled in the art, the precise position of the peaks may vary slightly between one machine and another, from one sample to another, or as a result of slight variations in measurement conditions utilised.

It is also stated in the preceding paragraphs that the amorphous form and the crystalline forms of compound of formula (I) provide X-ray powder diffraction patterns substantially the same as the X-ray powder diffraction patterns shown in FIGS. 1, 2, 3 and 4 and have substantially the most prominent peaks at the 2-theta angle values shown in tables 1, 2, 3 and 4. It shall be appreciated that the use of the term 'substantially' in this context is also intended to indicate that the 2-theta angle values of the X-ray powder diffraction patterns may vary slightly from one machine to another, from one sample to another, or as a result of slight variations in measurement conditions, so the peak positions shown in the figures or quoted in the tables are again not to be as absolute values.

In this regard, it is known in the art that an X-ray powder diffraction pattern may be obtained which has one or more measurement errors depending on measurement conditions (such as, for example, equipment and/or sample preparation). In particular, it is generally known that intensities in an X-ray powder diffraction pattern may vary depending on measurement conditions and sample preparation.

For example, persons skilled in the art of X-ray powder diffraction will realise that the relative intensity of peaks can be affected by, for example, grains above 30 microns in size and non-unitary aspect ratios, which may affect analysis of samples.

The skilled person will also realise that the position of reflections can be affected by the precise height at which the sample sits in the diffractometer and the zero calibration of the diffractometer. The surface planarity of the sample may also affect the result.

Hence a person skilled in the art will appreciate that the diffraction pattern data presented herein are not to be considered as absolute (for further information see "Fundamentals of Powder Diffraction and Structural Characterization", Pecharsky and Zavalij, Kluwer Academic Publishers, 2003). Therefore, it shall be understood that the amorphous form and the crystalline forms of compound of formula (I) described in the present invention are not limited to the amorphous and the crystals that provide X-ray powder diffraction patterns identical to the X-ray powder diffraction patterns shown in FIGS. 1, 2, 3 and 4 and any sample or batch of amorphous form or crystalline forms of compound of formula (I) providing X-ray powder diffraction patterns substantially the same as that shown in FIGS. 1, 2, 3 and 4 fall within the scope of the present invention. A person skilled in the art of X-ray powder diffraction is able to judge the substantial identity of X-ray powder diffraction patterns.

Generally, a measurement error of a diffraction angle in an X-ray powder diffractogram is about 2-theta=0.5 deg or less (or, more suitably, about 2-theta=0.2 deg or less) and such degree of a measurement error should be taken into account when considering the X-ray powder diffraction pattern in FIGS. 1, 2, 3, and 4 and when comparing the patterns or interpreting the peak positions referred to both in the text and in tables 1, 2, 3 and 4.

Therefore, where it is stated, for example, that the crystalline forms of compound of formula (I), have an X-ray powder diffraction pattern with at least one specific peak at about 2-theta=20.1 deg (or any one of the other mentioned angles) then this can be interpreted as being 2-theta=20.1 deg plus or minus 0.5 deg, or 2-theta=20.1 deg plus or minus 0.2 deg.

The X-ray diffraction diagrams of crystalline form 3, the amorphous form, crystalline form 1 and crystalline form 2 are reported in FIGS. 1, 2, 3 and 4 respectively. The X-ray diffraction peak positions of crystalline form 3, crystalline form 1 and crystalline form 2 are reported in tables 2, 3 and 4 respectively.

TABLE 2

Crystalline form 3 of the compound of formula (I)

| Position (Deg.) | Intensity (CPS) | Relative Intensity (%) |
|---|---|---|
| 7.1 | 369.8 | 20.4 |
| 7.7 | 50.8 | 2.8 |
| 8.4 | 398.3 | 22.0 |
| 9.4 | 45.0 | 2.5 |
| 10.5 | 1812.1 | 100.0 |
| 11.3 | 76.8 | 4.2 |
| 13.1 | 54.4 | 3.0 |
| 13.4 | 77.6 | 4.3 |
| 13.8 | 271.2 | 15.0 |
| 14.5 | 567.5 | 31.3 |
| 15.6 | 159.7 | 8.8 |
| 16.1 | 48.1 | 2.7 |
| 16.8 | 366.4 | 20.2 |
| 17.0 | 248.2 | 13.7 |
| 17.4 | 876.4 | 48.4 |
| 17.9 | 59.1 | 3.3 |
| 18.4 | 106.9 | 5.9 |
| 18.5 | 154.9 | 8.6 |
| 19.3 | 616.1 | 34.0 |
| 19.3 | 193.4 | 10.7 |
| 20.1 | 21.7 | 1.2 |
| 20.7 | 465.7 | 25.7 |
| 21.3 | 826.9 | 45.6 |
| 22.5 | 643.8 | 35.5 |
| 23.1 | 184.9 | 10.2 |
| 23.5 | 476.7 | 26.3 |
| 24.5 | 258.5 | 14.3 |
| 25.6 | 231.7 | 12.8 |
| 26.4 | 34.5 | 1.9 |
| 26.8 | 84.0 | 4.6 |
| 30.1 | 169.5 | 9.4 |
| 32.6 | 24.2 | 1.3 |
| 33.3 | 43.0 | 2.4 |
| 35.8 | 51.9 | 2.9 |

TABLE 3

Crystalline form 1 of the compound of formula (I)

| Position (Deg.) | Intensity (CPS) | Relative Intensity (%) |
|---|---|---|
| 4.1 | 79.6 | 10.7 |
| 4.8 | 453.4 | 61.0 |
| 7.3 | 28.7 | 3.9 |
| 7.5 | 137.4 | 18.5 |
| 8.1 | 56.1 | 7.6 |
| 8.9 | 52.9 | 7.1 |
| 9.2 | 15.8 | 2.1 |
| 9.8 | 61.3 | 8.3 |
| 11.1 | 67.8 | 9.1 |
| 13.0 | 80.0 | 10.8 |
| 13.5 | 71.0 | 9.5 |
| 13.8 | 38.2 | 5.1 |
| 14.6 | 16.5 | 2.2 |
| 15.2 | 158.7 | 21.4 |
| 16.2 | 743.3 | 100.0 |
| 17.4 | 347.9 | 46.8 |
| 17.8 | 93.1 | 12.5 |
| 18.2 | 7.5 | 1.0 |

TABLE 3-continued

Crystalline form 1 of the compound of formula (I)

| Position (Deg.) | Intensity (CPS) | Relative Intensity (%) |
|---|---|---|
| 18.7 | 548.3 | 73.8 |
| 19.5 | 155.8 | 21.0 |
| 20.1 | 655.0 | 88.1 |
| 20.5 | 194.4 | 26.2 |
| 21.1 | 22.1 | 3.0 |
| 21.8 | 30.7 | 4.1 |
| 22.3 | 391.8 | 52.7 |
| 23.0 | 138.6 | 18.6 |
| 23.3 | 164.5 | 22.1 |
| 23.9 | 24.9 | 3.4 |
| 24.4 | 102.2 | 13.7 |
| 24.7 | 38.3 | 5.2 |
| 25.0 | 184.9 | 24.9 |
| 25.5 | 81.7 | 11.0 |
| 26.2 | 40.2 | 5.4 |
| 27.2 | 30.8 | 4.2 |
| 27.3 | 26.0 | 3.5 |
| 29.1 | 18.1 | 2.4 |
| 29.5 | 30.3 | 4.1 |
| 30.1 | 10.4 | 1.4 |
| 30.6 | 22.0 | 3.0 |
| 31.5 | 36.5 | 4.9 |
| 36.6 | 42.6 | 5.7 |

TABLE 4

Crystalline form 2 of the compound of formula (I)

| Position (Deg.) | Intensity (CPS) | Relative Intensity (%) |
|---|---|---|
| 6.6 | 340.4 | 7.7 |
| 9.8 | 91.2 | 2.1 |
| 10.5 | 504.9 | 11.4 |
| 11.1 | 842.3 | 19.0 |
| 12.4 | 49.2 | 1.1 |
| 14.3 | 1451.9 | 32.8 |
| 15.3 | 975.7 | 22.0 |
| 15.9 | 159.3 | 3.6 |
| 16.9 | 256.8 | 5.8 |
| 17.8 | 400.5 | 9.0 |
| 18.4 | 2750.6 | 62.1 |
| 19.0 | 1244.8 | 28.1 |
| 19.9 | 1595.9 | 36.0 |
| 20.2 | 375.6 | 8.5 |
| 21.0 | 268.6 | 6.1 |
| 21.3 | 555.6 | 12.5 |
| 21.8 | 4433.2 | 100.0 |
| 22.3 | 1128.6 | 25.5 |
| 22.5 | 597.7 | 13.5 |
| 23.2 | 135.0 | 3.0 |
| 23.6 | 1110.6 | 25.1 |
| 24.9 | 310.3 | 7.0 |
| 25.1 | 129.6 | 2.9 |
| 25.5 | 213.6 | 4.8 |
| 25.9 | 85.6 | 1.9 |
| 26.4 | 1066.3 | 24.1 |
| 27.6 | 194.7 | 4.4 |
| 28.1 | 122.6 | 2.8 |
| 28.7 | 141.3 | 3.2 |
| 29.0 | 45.6 | 1.0 |
| 29.3 | 152.5 | 3.4 |
| 29.5 | 91.2 | 2.1 |
| 30.0 | 376.4 | 8.5 |
| 30.4 | 142.4 | 3.2 |
| 30.8 | 203.3 | 4.6 |
| 31.5 | 46.6 | 1.1 |
| 31.9 | 243.7 | 5.5 |
| 32.2 | 42.6 | 1.0 |
| 32.4 | 65.8 | 1.5 |
| 33.0 | 281.4 | 6.4 |
| 33.6 | 54.2 | 1.2 |

TABLE 4-continued

Crystalline form 2 of the compound of formula (I)

| Position (Deg.) | Intensity (CPS) | Relative Intensity (%) |
|---|---|---|
| 34.7 | 135.5 | 3.1 |
| 34.9 | 173.7 | 3.9 |
| 38.1 | 85.6 | 1.9 |
| 38.4 | 92.6 | 2.1 |

Example 3

Analytical Results by Means of Differential Scanning Calorimetry (DSC)

DSC analyses were carried out with a Mettler Toledo Star system apparatus. Aluminum DSC pans were loaded with 2-4 mg of sample. The temperature range of the analyses was between 25° C. and a maximum value of 300° C. The samples were analyzed under nitrogen static condition at a heating rate of 10° C./min.

FIG. 5 reports DSC thermograms of the amorphous form, crystalline form 1 and crystalline form 2. The observed melting endotherm for crystalline form 1 is at approximately in the range 188° C.-196° C. (peak temperature) with Delta H in the range 54-64 J/g. The observed melting endotherm for crystalline form 2 is at approximately in the range 197° C.-198.5° C. (peak temperature) with Delta H in the range 72-78.5 J/g. It be understood that the onset and/or peak temperature values of the DSC may vary slightly from one apparatus to another, one method to another or from one sample to another, and so the values quoted are not to be considered as absolute. In fact, observed temperatures will depend on the rate of temperature change as well as sample preparation technique and the particular instrument employed. It will be estimated and taken into account that the temperature values obtained applying such different conditions may vary by plus or minus about 4° C.

Example 4

Analytical Results by Means of Dynamic Vapour Sorption (DVS)

The observed water uptake was investigated by submitting a sample of such substances to a hygroscopicity test by means of a DVS 1000 (SMS). The apparatus is a "controlled atmosphere microbalance" where the weighed sample is exposed to programmed variations of the relative humidity (RH) at a constant and controlled temperature. The measured parameters (weight, time and RH), reported in Excel worksheets, allow obtaining hygroscopicity curves over the tested RH range. For example, sorption/desorption cycles between 0% and 90% RH can be performed at controlled temperature of 25° C. Progressive variations of RH can be, for example, of 10% and 3% and are operated by the software at the equilibration of the sample weight. This condition can be defined at a constant rate of percent weight variation such as, for example, 0.005%/min.

FIG. 6 reports the DVS profiles of the amorphous form, crystalline form 1 and crystalline form 2 of the compound of formula (I). Relative Humidity (RH, %) values are reported on the x-axis while Change in Mass (%) is reported on the y axis. The curves are related to the sorption step between 0% RH and 90% RH at 25° C.

The experimental results show that crystalline form 1 and crystalline form 2 of the compound (I) are respectively characterized by water uptakes of 0.6% and 0.2% at 25° C./90% RH. Such water uptakes are reversible by lowering RH at constant temperature of 25° C. The crystalline forms 1 and 2 of the compound (I) can be considered of low hygroscopicity.

The experimental results also show that the amorphous form of the compound (I) is characterized by a water uptake of 2.5% at 25° C./90% RH that is reversible by lowering RH at constant temperature of 25° C. The amorphus form of the compound (I) shows higher hygroscopicity than the crystalline forms 1 and 2. The water uptake of the amorphous form of the compound (I) is higher than the crystalline forms 1 and 2. As a further aspect, the water uptake of the amorphus form of the compound (I) is greater than 1% from RH values that are lower than 30% RH with a subsequent slope increase in the region of high RH values.

Example 5

Analytical Results by Means of Thermogravimetric Analysis (TGA)

TGA analyses were carried out with a Perkin-Elmer TGA-7 apparatus. Aluminum DSC pans were loaded with 5÷10 mg of sample. The temperature range of the analyses was between 30° and a maximum value of about 250° C. The samples were analyzed under nitrogen flow (to eliminate oxidative and pyrolitic effects) at a heating rate of 2° C./min.

Example 6

NMR Analyses

The $^1$H NMR experiments were performed at a constant temperature of 28° C., on a Varian Inova 500 spectrometer for the crystalline form 3 sample (see FIG. 8) and at a constant temperature of 28° C., on a Varian Inova 400 spectrometer for the crystalline form 1 sample (see FIG. 7). A small amount of each sample was dissolved in 0.75 mL of DMSO-$d_6$ and transferred into a 5-mm NMR tube for subsequent analysis. As the same $^1$H NMR spectrum is obtained from different crystalline forms, i.e. crystalline form 1 and 2 have the same $^1$H NMR spectrum, only the spectrum of the crystalline form 1 is reported. The spectrum of crystalline form 3 is reported only to show the presence of residual solvents whose signals are clearly distinguished from the signals of the product and are highlighted by arrows in FIG. 8.

Example 7

Percent Compositions of a Formulation for Oral Use

| Ingredient | Range % |
| --- | --- |
| Crystalline form 2, | 20 ÷ 60 |
| Mannitol | 20 ÷ 60 |
| Pregelatinized Starch | 5 ÷ 50 |

-continued

| Ingredient | Range % |
| --- | --- |
| Colloidal silicon dioxide | 0.2 ÷ 2 |
| Magnesium stearate | 0.5 ÷ 2 |

What is claimed is:

1. A method of treating a disease in a mammal, comprising administering to said mammal a therapeutically effective amount of an unsolvated crystalline form 2 of N-[5-(3,5-difluorobenzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising a peak at a 2-theta value of about 10.5±0.5 degrees, and wherein said disease is selected from the group consisting of non-small cell lung cancer (NSCLC), colorectal cancer (CRC), neuroblastoma, medulloblastoma and melanoma.

2. The method according to claim 1, wherein said x-ray powder diffraction pattern of said unsolvated crystalline form 2 of N-[5-(3,5-difluorobenzyl)-1H-indazol-3-yl]-4-(4-methyl-piperazin-1-yl)-2-(tetrahydro-pyran-4-ylamino)-benzamide further comprises a peak at a 2-theta value of about 11.1±0.5 degrees.

3. The method according to claim 2, wherein said x-ray powder diffraction pattern of said unsolvated crystalline form 2 of N-[5-(3,5-difluorobenzyl)-1H-indazol-3-yl]-4-(4-methyl-piperazin-1-yl)-2-(tetrahydro-pyran-4-ylamino)-benzamide further comprises peaks at 2-theta values of about 14.3±0.5 degrees, 18.4±0.5 degrees, and 21.8±0.5 degrees.

4. The method according to claim 1, wherein said unsolvated crystalline form 2 of N-[5-(3,5-difluorobenzyl)-1H-indazol-3-yl]-4-(4-methyl-piperazin-1-yl)-2-(tetrahydro-pyran-4-ylamino)-benzamide is further characterized by exhibiting a peak in a differential scanning calorimetry scan of from about 197° C. to about 198.5° C.

5. The method according to claim 1, wherein said mammal is a human.

6. A method of treating a disease in a mammal, comprising administering to said mammal a pharmaceutical composition comprising at least one pharmaceutically acceptable excipient and a therapeutically effective amount of an unsolvated crystalline form 2 of N-[5-(3,5-difluorobenzyl)-1H-indazol-3-yl]-4-(4-methyl-piperazin-1-yl)-2-(tetrahydro-pyran-4-ylamino)-benzamide, wherein said crystalline form is characterized by an x-ray powder diffraction pattern comprising a peak at a 2-theta value of about 10.5±0.5 degrees, and wherein said disease is selected from the group consisting of non-small cell lung cancer (NSCLC), colorectal cancer (CRC), neuroblastoma, medulloblastoma and melanoma.

7. The method according to claim 6, wherein said x-ray powder diffraction pattern of said unsolvated crystalline form 2 of N-[5-(3,5-difluorobenzyl)-1H-indazol-3-yl]-4-(4-methyl-piperazin-1-yl)-2-(tetrahydro-pyran-4-ylamino)-benzamide further comprises a peak at a 2-theta value of about 11.1±0.5 degrees.

8. The method according to claim 7, wherein said x-ray powder diffraction pattern of said unsolvated crystalline form 2 of N-[5-(3,5-difluorobenzyl)-1H-indazol-3-yl]-4-(4-methyl-piperazin-1-yl)-2-(tetrahydro-pyran-4-ylamino)-benzamide further comprises peaks at 2-theta values of about 14.3±0.5 degrees, 18.4±0.5 degrees, and 21.8±0.5 degrees.

9. The method according to claim 6, wherein said unsolvated crystalline form 2 of N-[5-(3,5-difluorobenzyl)-1H-indazol-3-yl]-4-(4-methyl-piperazin-1-yl)-2-(tetrahydro-pyran-4-ylamino)-benzamide is further characterized by exhibiting a peak in a differential scanning calorimetry scan of from about 197° C. to about 198.5° C.

10. The method according to claim 6, wherein said mammal is a human.

* * * * *